United States Patent
Sakura, Jr.

[11] Patent Number: 6,099,565
[45] Date of Patent: Aug. 8, 2000

[54] PROSTHETIC TISSUE IMPLANT AND FILLER THEREFOR

[76] Inventor: Chester Y. Sakura, Jr., 7483 Prairie, NE., Albuquerque, N. Mex. 87109

[21] Appl. No.: 08/478,277

[22] Filed: Jun. 7, 1995

[51] Int. Cl.$^7$ .................................................. A61F 2/12
[52] U.S. Cl. ................................................................ 623/8
[58] Field of Search .................................. 623/11, 12, 7, 623/8, 66, 37, 36, 17

[56] References Cited

U.S. PATENT DOCUMENTS

| | | | |
|---|---|---|---|
| 3,986,213 | 10/1976 | Lynch | 623/8 |
| 4,605,412 | 8/1986 | La Forest et al. | 623/8 |
| 4,955,907 | 9/1990 | Ledergerber | 623/8 |
| 5,192,326 | 3/1993 | Bao et al. | 623/17 |
| 5,246,454 | 9/1993 | Peterson | 623/8 |
| 5,447,535 | 9/1995 | Muller | 623/8 |
| 5,464,443 | 11/1995 | Wilson | 623/36 |
| 5,534,023 | 7/1996 | Henley | 623/8 |

*Primary Examiner*—David J. Isabella
*Attorney, Agent, or Firm*—Woodard, Emhardt, Naughton, Moriarty & McNett

[57] ABSTRACT

A biologically compatible human breast implant is disclosed which has improved natural feel and is resistant to leakage. In the disclosed implant, a large quantity of small, pliable hollow spheroids of polymeric material are used as a filler within the implant shell. The hollow spheroids are partially filled with a fluid when in an uncompressed state, and provide a cushioning effect by being compressible to the point where the resulting reduction in the interior space causes the interior to become essentially filled by the fluid and where further compression is resisted due to the relative non-compressibility of the contained fluid. The described spheroids are made of silicone rubber and are partially filled with saline solution. The spheroids have an outside diameter of from about 1 mm to 5 mm, an outer wall thickness of about 75 to 225 microns, and the fluid contained therein is filled to about 80 to 90% of capacity when the spheroids are in their naturally uncompressed spherical state.

28 Claims, 1 Drawing Sheet

PROSTHETIC TISSUE IMPLANT AND FILLER THEREFOR

TECHNICAL FIELD OF THE INVENTION

The present invention relates generally to prosthetic tissue implants, such as breast implants. More particularly, the present invention relates to filler that is placed within the outer shell of the implant.

BACKGROUND OF THE INVENTION

Breast implants are commonly used to replace or augment breast tissue. Typically, such implants are made from a shell of soft and flexible biocompatible material which is filled with a fluid, such as a saline solution, or a polysiloxane or a silicone gel.

It is naturally desirable for a breast implant to match the weight and feel of the tissue being replaced or augmented. Implants which have saline solution as the filler material have been lacking in this regard because the saline solution tends to flow too freely within the implant, thereby reducing the naturalness of the implant's feel. Saline-containing implants also have a disadvantage in that leaks in the outer shell or in the valving mechanism can occur which lead to the undesirable spread of the filler medium within the body as well as deflation of the implant itself. In some implants, saline solution has been replaced with a gel to more closely resemble the feel of the tissue and to reduce the adverse effects of leakage.

It has also been known to incorporate various interior structures within the implant in addition to or in lieu of liquid as filler for the implant. For instance, U.S. Pat. No. 5,246,454 to Peterson discloses a breast implant in which flat, disc shaped pouches filled with saline solution comprise the interior structure of the implant. Also, U.S. Pat. Nos. 5,007,940, 5,116,387 and 5,158,573 to Berg disclose the use of discrete polymeric bodies as tissue replacement material. The polymeric bodies may be injected into the body to form an in situ implant, or may be used as filler within an outer implant shell. The bodies are made of silicone rubber or a water swellable hydrogel, specifically a partially hydrolyzed polyacronitrile, and are described to have reversible deformity of about 20 to 75% of their unstressed outer diameter and a lubricious surface.

There is a need for an improved breast implant which will retain the natural feel of the tissue being replaced, and which will also substantially reduce or eliminate the probability of leakage. Ideally, the implant will also not deflate if a leak should occur in the outer shell of the implant. The present invention is directed toward meeting these needs.

SUMMARY OF THE INVENTION

The present invention relates to a new prosthetic tissue implant which has improved natural feel and is resistant to leakage. In an implant according to the present invention, a large quantity of small, elastically compressible hollow spheroids of polymeric material are used as a filler within the implant shell. The hollow spheroids are partially filled with a fluid when in an uncompressed state, and provide a cushioning effect by being compressible to the point where the resulting reduction in the interior space causes the interior to become essentially filled by the fluid and where further compression is resisted due to the relative non-compressibility of the contained fluid. As a result, the implant provides a true natural feel in that it provides an initial "give" upon the application of pressure but then gives increased resistance due to the fluid within the spheroids in their compressed state. The degree of responsive resistance of the individual spheroids is determinable at manufacture by the selection of the material and dimensions for the spheroids, and the degree to which the spheroids are filled when uncompressed. The overall "feel" of the implant itself is easily controlled by the selection of the number of spheroids that are placed within the implant shell. In the following described preferred embodiment, the spheroids are made of silicone rubber and are partially filled with saline solution. The spheroids have an outside diameter of from about 1 mm to 5 mm, an outer wall thickness of about 75 to 225 microns, and the fluid contained therein is filled to about 80 to 90% of capacity when the spheroids are in their naturally uncompressed spherical state.

BRIEF DESCRIPTION OF THE DRAWINGS

FIG. 1a is a cross-sectional view of breast implant 20 in its naturally uncompressed shape. FIG. 1b is a cross-sectional view of the breast implant of FIG. 1a, with a portion of implant 20 being compressed by finger 99.

FIG. 2a is an enlarged cross-sectional view of spheroid 10 in an uncompressed state in which it is partially filled by fluid 14. FIG. 2b is a cross-sectional view of the spheroid 10' in a compressed state in which the interior space within spheroid 10' is essentially filled by fluid 14' and where the application of further pressure upon spheroid 10' will be met with increased resistance owing to the relative non-compressibility of fluid 14'.

DESCRIPTION OF THE PREFERRED EMBODIMENT

Figure 1A:
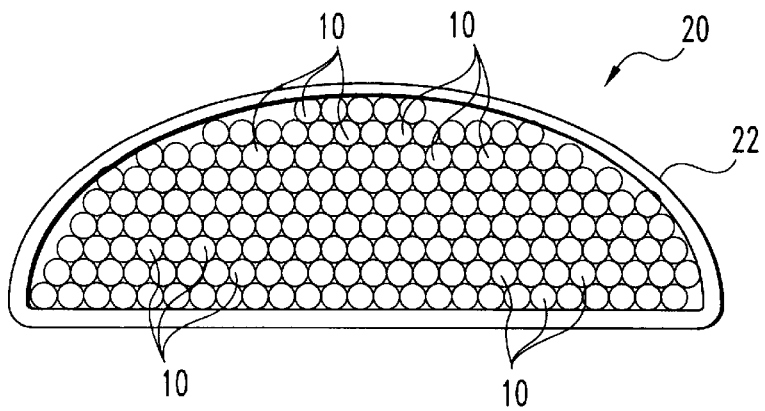
FIGS. 1a and 1b are cross-sectional views of a breast implant 20 according to the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

As shown and described herein, the present invention teaches the utilizing of a large quantity of small, elastically compressible hollow spheroids of polymeric material as filler for a soft tissue prosthetic implant. The spheroids are partially filled with a biocompatible liquid when in an uncompressed state, and are elastically compressible to the extent such that the resulting reduction in interior space causes the interior space to become essentially filled by the fluid therein and where further compression is then subject to increased resistance due to the relative non-compressibility of the contained fluid. A soft tissue implant incorporating this unique structure simulates the feel of natural tissue by first relatively compliantly deforming in response to the application of pressure and then giving increased resistance in response to increased pressure when the resulting reduction in the interior space within the spheroids causes their interiors to become filled by the contained fluid. The degree of responsive resistance of the individual spheroids is determinable at manufacture by the selection of the material and dimensions for the spheroids, and the degree to which the spheroids are filled when uncompressed. The overall "feel" of the implant itself is easily controlled by the number of spheroids that are placed within the implant shell.

Referring now to FIG. 1a, there is illustrated a breast implant of the present invention indicated generally at 20. Implant 20 includes an outer shell 22 of soft, flexible, fluid impermeable, rupture preventing material such as silicone rubber, and is filled with a large quantity of elastically compressible spheroids 10 which act as filler for implant 20. As described in further detail below, spheroids 10 are made of hollow spheres of silicone rubber, which are partially filled with a biocompatible liquid, such are saline solution.

Figure 2A:
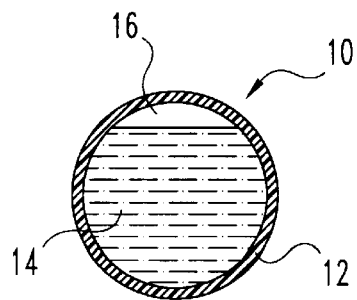
FIGS. 2a and 2b are enlarged cross-sectional views of sample spheroids 10 and 10' used as filler within implant 20.

Referring next to FIG. 2a, there is illustrated a cross-sectional view of a sample spheroid 10 used as implant filler for implant 20 in FIG. 1a in a natural uncompressed state. Spheroid 10 includes an elastically compressible hollow ball 12 of biocompatible polymeric material, such as silicone, which is formed in a spherical shape when uncompressed, and which is partially filled with a biocompatible liquid 14, such as saline solution. When uncompressed as shown in FIG. 2a, hollow ball 12 is spherical in shape and is partially filled to about 80–90% of its total capacity by liquid 14, leaving an unfilled space or void 16 therein. Optimally, the exterior diameter of ball 12 should be in the range of about 1–5 mm, and more preferably in the range of 2–4 mm. The wall thickness of hollow ball 12 is preferably in the range of approximately 75 to 225 microns.

Figure 1B:
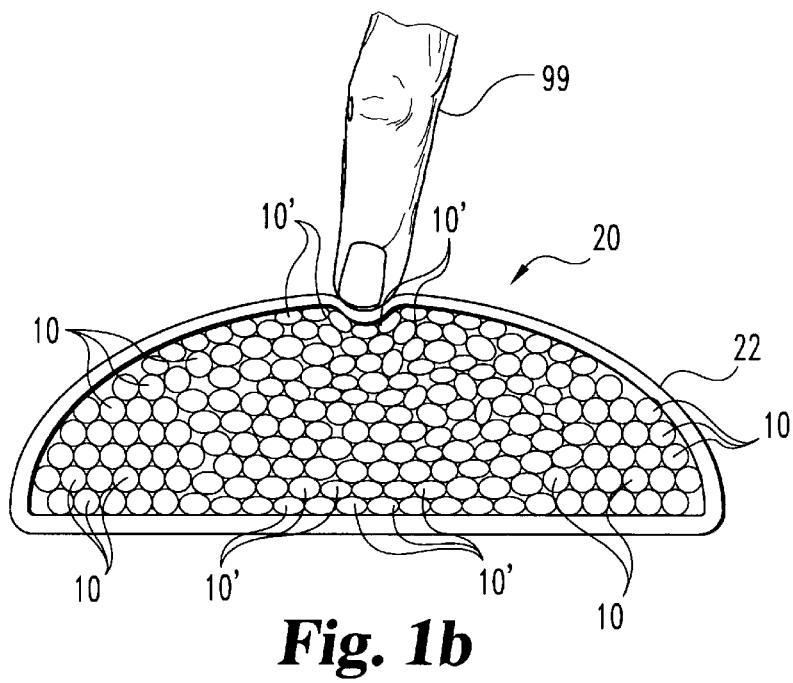

The elastic deformability of the implant 20 of the present invention in response to applied pressure against implant 20 is illustrated in FIG. 1b. When subjected to external forces, such as pressure from finger 99, implant 20 at first readily deforms to an extent, but then exhibits a firmness in resistance to further deformation as the interior spaces within spheroids 10' reduces to the point where fluid therein fills the interior space within spheroids 10' thereby resulting in increased resistance to the further application of pressure by finger 99. This initial relative compliability, followed by a degree of increased firmness simulates the behavior of natural breast tissue. Thus, as illustrated in FIG. 1b, spheroids 10' in proximity to the application of pressure by finger 99 are compressed to the point where there is increased resistance to further pressure from finger 99 owing to the fluid contained in spheroids 10'. The resulting "give" to the initial application of pressure followed by increased resistance to the application of increased pressure gives the implant a natural and realistic feel.

Figure 2B:
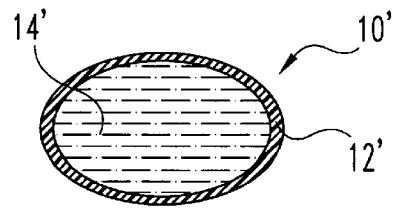

FIG. 2b is a cross-sectional view of a sample spheroid 10' in a compressed state. In FIG. 2b, it is seen that the compression of ball 12 as a result of the application of pressure thereon has reduced the interior space therein to the point where ball 12' has become essentially filled by fluid 14'. When spheroid 10' has been so compressed, there is resulting increased resistance to the application of further pressure upon spheroid 10' owing to the relative non-compressibility of fluid 14' contained therein.

It is to be appreciated that relative overall firmness of implant 20 can be controlled by adjusting the quantity of spheroids 10 within implant 20. The feel can thus be individually adjusted by adding or removing some of spheroids 10 from within implant 20, which can be done by the surgeon or an assistant when the implant procedure is to be performed. In this regard, it is contemplated that spheroids 10 could be selectively added or removed through a tube placed through a standard valving mechanism in implant 20.

It is to be appreciated by those skilled in the art that the principles of the present invention, as described above, are applicable to soft tissue body prostheses for other areas of the body as well as for the breast. Also, it is to be observed that hollow filler bodies used in the present invention need not necessarily be generally spheroidal in shape, or specifically spherical when in their uncompressed natural state, but might be formed in other shapes as well and still fall within the spirit of the invention. It is to be further understood that space or void 16 may or may not be a vacuum but might include some air or other gas therein, so that the effect of the increased resistance owing to the contained fluid occurs as the interior space becomes essentially filled by the contained fluid, there being some residual space remaining unfilled by the liquid which is occupied by the resulting compressed gas.

Accordingly, while the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A prosthetic human breast implant, comprising:
   an outer shell of polymeric material having a cavity therein, said outer shell being sized and shaped for augmenting, reshaping or replacing human breast tissue;
   a plurality of hollow bodies of biologically compatible elastically deformable material contained within said cavity, each of said hollow bodies containing biologically compatible liquid material sealed therein, each of said hollow bodies being partially filled with said fluid when in an uncompressed state, wherein said bodies are elastically compressible to the extent where the resulting reduction in the interior space within said hollow bodies causes the interior to become essentially filled by said fluid and where further compression is resisted due to the relative non-compressibility of the contained fluid.

2. The prosthetic human breast implant of claim 1 in which said hollow bodies are generally spheroidal in shape when in an uncompressed state.

3. The prosthetic human breast implant of claim 1 wherein each of said hollow bodies are partially filled in the range of 80–90% of capacity by said fluid when in an uncompressed state.

4. The prosthetic human breast implant of claim 1, wherein said hollow bodies are made of silicone rubber.

5. The prosthetic human breast implant of claim 1, wherein said liquid material is saline solution.

6. The prosthetic human breast implant of claim 1, wherein said hollow bodies have an outside diameter in the range of from about 1 mm to 5 mm.

7. The prosthetic human breast implant of claim 1, wherein said hollow bodies have a wall thickness in the range of about 75 to 250 microns.

8. The prosthetic human breast implant of claim 1, wherein said hollow bodies are spherical in shape when in an uncompressed state.

9. A prosthetic implant, comprising:
   an outer shell of polymeric material having a cavity therein; and
   filler contained within said cavity in said outer shell, said filler including a plurality of hollow structured bodies of biologically compatible elastically compressible material, each of said bodies containing biologically compatible liquid material sealed therein and being partially filled with said liquid material leaving interior space within said bodies unfilled by said liquid material when said bodies are in an uncompressed state, wherein said bodies are elastically compressible to the extent where the resulting reduction in the interior space within said bodies causes the interior to become essentially filled by said liquid material and where further compression is resisted due to the relative non-compressibility of the contained liquid material;

further wherein said hollow bodies are generally spherical in shape when in an uncompressed state.

10. The prosthetic implant of claim 9, wherein each of said hollow bodies are filled in the range of 80–90% of capacity by said fluid when in an uncompressed state.

11. The prosthetic implant of claim 9, wherein said hollow bodies are made of silicone rubber.

12. The prosthetic implant of claim 9, wherein said liquid material is saline solution.

13. The prosthetic implant of claim 9, wherein said hollow bodies have an outside diameter in the range of 1 mm to 5 mm.

14. The prosthetic implant of claim 9, wherein said hollow bodies have an outside diameter in the range of from about 2 mm to 4 mm.

15. The prosthetic implant of claim 9, wherein said hollow bodies have a thickness in the range of about 75 to 250 microns.

16. Filler for a prosthetic implant comprising hollow spheroids of biologically compatible elastically deformable material each containing biologically compatible liquid material sealed therein, each of said spheroids being partially filled with said fluid when in an uncompressed state, wherein said spheroids are elastically compressible to the extent where the resulting reduction in the interior space within said spheroids causes the interior to become essentially filled by said fluid and where further compression is resisted due to the relative non-compressibility of the contained fluid.

17. The prosthetic implant filler of claim 16 wherein each of said spheroids are partially filled in the range of 80–90% of capacity by said fluid when in an uncompressed state.

18. The prosthetic implant filler of claim 16, wherein said spheroids are made of silicone rubber.

19. The prosthetic implant filler of claim 16, wherein said liquid material is saline solution.

20. The prosthetic implant of claim 16, wherein said hollow bodies have an outside diameter in the range of 1 mm to 5 mm.

21. The prosthetic implant filler of claim 16, wherein said spheroids have a wall thickness in the range of about 75 to 225 microns.

22. The prosthetic implant filler of claim 16, wherein said hollow spheroids are spherical in shape when in an uncompressed state.

23. Filler for a prosthetic implant comprising a plurality of hollow structured bodies of biologically compatible elastically compressible material, each of said bodies containing biologically compatible liquid material sealed therein being partially filled with said liquid material leaving interior space within said bodies unfilled by said liquid material when said bodies are in an uncompressed state, wherein said bodies are elastically compressible to the extent where the resulting reduction in the interior space within said bodies causes the interior to become essentially filled by the liquid material and where further compression is resisted due to the relative non-compressibility of the contained liquid material;

further wherein said hollow bodies have an outside diameter in a range of about 1 mm to about 5 mm.

24. The prosthetic implant filler of claim 23 wherein each of said hollow bodies are partially filled in the range of 80–90% of capacity by said fluid when in an uncompressed state.

25. The prosthetic implant filler of claim 23, wherein said hollow bodies are made of silicone rubber.

26. The prosthetic implant filler of claim 23, wherein said liquid material is saline solution.

27. The prosthetic implant of claim 23, wherein said hollow bodies have a wall thickness in the range of about 75 to 225 microns.

28. The prosthetic implant of claim 23, wherein said hollow bodies have an outside diameter in the range of from about 2 mm to 4 mm.

* * * * *